United States Patent [19]

Majer et al.

[11] 4,006,171
[45] Feb. 1, 1977

[54] PROCESS FOR THE PREPARATION OF HALOGENOANTHRAQUINONES

[75] Inventors: Norbert Majer, Schildgen; Hans-Samuel Bien, Burscheid; Helmut Judat, Langenfeld; Armin Lieberam, Cologne, all of Germany

[73] Assignee: Bayer Aktiengesellschaft, Leverkusen, Germany

[22] Filed: Oct. 24, 1975

[21] Appl. No.: 625,725

[30] Foreign Application Priority Data

Nov. 2, 1974  Germany .......................... 2452014
Nov. 23, 1974 Germany .......................... 2455587

[52] U.S. Cl. .............................................. 260/384
[51] Int. Cl.$^2$ ........................................ C07C 49/68
[58] Field of Search .................................. 260/384

[56] References Cited

FOREIGN PATENTS OR APPLICATIONS

| 128,845 | 7/1900 | Germany |
| 254,450 | 8/1911 | Germany |
| 252,578 | 11/1911 | Germany |
| 178,390 | 9/1966 | U.S.S.R. |

Primary Examiner—Arthur P. Demers
Attorney, Agent, or Firm—Burgess, Dinklage & Sprung

[57] ABSTRACT

A process for the preparation of a chloroanthraquinone or a bromoanthraquinone comprising treating a molten mixture of at least one nitroanthraquinone and diluent with halogen at a temperature of about 180 to 300° C, the diluent being present in at least about 10% by weight of the mixture and comprising at least one chloroanthraquinone or bromoanthraquinone. The diluent may correspond to the halogenoanthraquinone obtained from the nitroanthraquinone by replacement of the nitro group. A portion of the product can be recycled as diluent for further reaction.

13 Claims, No Drawings

PROCESS FOR THE PREPARATION OF HALOGENOANTHRAQUINONES

The present invention relates to an improved process for the preparation of chloroanthraquinones or bromoanthraquinones by the action of chlorine or bromine on corresponding nitroanthraquinones.

It is known from German Patent Specifications Nos. 252,578 and 254,450 to prepare chloroanthraquinones by treating nitroanthraquinones in inert organic solvents with elementary chlorine at temperatures of from 160° to 170° C. However, according to F. H. Day in J. Chem. Soc. (1939) page 817 the good yields of chloroanthraquinones allegedly obtained according to this old process could not be reproduced.

Another process for the preparation of chloroanthraquinones has been disclosed more recently in U.S.S.R. Patent Specification 178,390 in which nitroanthraquinones are chlorinated in bulk and as a mixture with sodium chloride at temperatures of from 270° to 290° C. However, when the applicants repeated this process it was also not possible to reproduce the high yields of about 90% reported in this publication.

It has now been found that chloroanthrachinones and bromoanthraquinones are obtained in a simple manner and in reproducibly good yields and relatively high purity when a melt of a mixture of a nitroanthraquinone, or of a mixture of nitroanthraquinones, and a chloroanthraquinone or bromoanthraquinone, or a mixture of chloroanthraquinones or bromoanthraquinones, the amount of halogenoanthraquinones, which serve as the diluent, being at least 10 per cent by weight, is initially introduced and a halogen is allowed to act on this melt at 180° to 300° C, preferably 220° to 280° C.

A particular process variant is characterised in that those chloroanthraquinones and bromoanthraquinones which are derived from the nitroanthraquinones employed by substituting chlorine or bromine for the nitro group or groups, are used as the diluent.

The mixing ratio of nitroanthraquinone to halogenoanthraquinone, which must be set up at the start of the reaction, depends on the properties of the melt of the nitroanthraquinones. Advantageously, the ratio is so selected that a melt which has a low viscosity and which can be stirred or pumped easily is formed, e. g. a viscosity of less than about 10 centipoise at 180° C. For the discontinuous procedure, mixtures which contain about 10 to 50 per cent by weight of a nitroanthraquinone (remainder: halogenoanthraquinone) are generally employed.

For the continuous procedure, technical grade or pure chloroanthraquinone is initially introduced in the molten form and an amount of a corresponding mixture of nitroanthraquinone and halogenoanthraquinone is metered in, say by recirculating a corresponding amount of halogenoanthraquinone, such that it reacts in the desired manner with the halogen which is passed in. The concentration of halogenoanthraquinone in the melt where it is first contacted by halogen advantageously is at least about 10% by weight, and preferably at least about 50% by weight. The concentration will rise in downstream direction of the melt and will approach 100%, the exact value depending upon the size of the reactor, the number of reaction stages, and the like.

When actually carrying out the discontinuous variant of the process according to the invention, the procedure is appropriately such that a mixture of a nitroanthraquinone and the corresponding halogenoanthraquinone (for example 1,8-dinitroanthraquinone and 1,8-dichloroanthraquinone), the ratio of these components which favors the formation of a melt of low viscosity having been determined in preliminary tests, is heated, by supplying heat from outside, to the required reaction temperature and the heat of reaction which is evolved is then removed by suitable cooling and metering of the stream of halogen, so that the desired reaction temperature is kept constant and no excess halogen escapes from the reaction vessel.

The nitrous waste gases, which are substantially free from oxygen and chlorine, are freed, in a condenser, from halogenoanthraquinone which has been carried over and are then either reduced catalytically, or worked up to give nitric acid, in the customary manner.

The reaction is complete as soon as no further nitrous gases are evolved and no nitroanthraquinones can be detected, for example, by thin layer chromatography or gas chromatography.

Working up of the reaction batch is simple and can be carried out in the customary manner. For example, the melt can be allowed to solidify by cooling and the product thus obtained can be comminuted. In the simplest case, the reaction batch is poured onto metal sheets or into vats and the product is allowed to solidify. Of course, it is also possible to use a flaking drum or other suitable equipment.

When the new process is carried out continuously, which is advantageously effected in an apparatus in which the gas and the melt are conducted in counter current, e. g. in a so-called bubble column as described in German Published Specification No. 2.331.195. However, any other piece of equipment of this type is suitable, e. g. a cascade of stirred vessels. The reaction melt is fed, for example, to a flaking drum for working up.

The new process is suitable for replacing the nitro groups in mononitroanthraquinones and dinitroanthraquinones, and in derivatives thereof having substituents which are preferably inert under the halogenation conditions, such as hydroxyl, carboxyl, fluorine, chlorine, bromine or mercapto, by halogen, preferably chlorine.

In principle, however, the nitroanthraquinones can also possess other substituents, insofar as a change in these is taken into account or is even desired.

Examples of such substituents are lower alkoxy groups and carboxylic acid ester groups, which are converted into hydroxyl groups and carboxyl groups respectively, and also lower alkyl groups (preferably methyl groups), which are wholly or partially halogenated and optionally converted, after appropriate hydrolysis, into aldehyde groups or carboxylic acid groups, and sulfonic acid groups and sulfonic acid ester groups, which are wholly or partially replaced by halogen, and also alkylmercapto and arylmercapto groups, which are split to free mercapto groups.

Suitable nitroanthraquinones which can be employed in the process according to the invention are: 1-nitroanthraquinone, 1,5-, 1,6-, 1,7-, 1,8-, 2,3-, 2,6- or 2,7-dinitroanthraquinone (or mixtures thereof, preferably mixtures such as are obtained from industrial mononitration or dinitration of anthraquinone as described in U.S. Pat. No. 3,818,052 (German Published Specification DOS 2,143,253) and German DOS 2,306,611 (Belgian Pat. No. 810,771) and DOS 2,256,664 (Belgian Pat. No. 807,383)), 1-nitro-4,5-dichloroanthraquinone, 1-chloro-2-nitroanthraquinone, 1-nitro-5-chloroanthraquinone, 1-nitro-6-chloroanthraquinone, 1-nitro-7-chloroanthraquinone, 1-nitro-8-chloroanthraquinone, 1-nitroanthraquinone-2-carboxylic acid, 1-methoxy-4-nitroanthraquinone, 1-hydroxy-4-nitroanthraquinone and 2-nitro-3-methylanthraquinone.

The chloroanthraquinones and bromoanthraquinones employed as diluents can be obtained by conventional means, for example by "Fischering" corresponding anthraquinonesulfonic acids (compare Ullman, Encyklopadie der technischen Chemie (Ullmann's Encyclopaedia of Industrial Chemistry), 4th edition (1973), volume 7, page 589) and can optionally be mixed appropriately, say when using mixtures of nitroanthraquinones.

In addition to the advantages already mentioned with regard to improved yield and possibly higher purity, the new process is distinguished, compared with the known solvent processes, by the simpler working up, shorter reaction times and overall, also because the solvent is omitted, by lower costs.

The process according to the invention also has a number of additional advantages compared with the previously known process for the halogenation of nitroanthraquinones in bulk, such as shortened reaction time, lower power consumption, fewer problems with regard to outgoing air (no escape of halogen and/or nitrosyl chloride or nitrosyl bromide), simpler and less hazardous handling (the reaction mixture is of low viscosity from the start and the course of the reaction can thus be controlled well) and the possibility for a continuous procedure.

The process products obtained are known, valuable starting materials for the preparation of vat dyestuffs (compare, for example, Ullmann, see above, page 631), of acid wool dyestuffs, for which they are, for example, reacted in a manner which is in itself known with amines and then sulfated (U.S. Pat. No. 2,605,269), and of dispersion dyestuffs, for which they are, for example, reacted in a manner which is in itself known with amines (German Published Specification DOS No. 2.050.961), thiophenols (British Patent Specification No. 1.081,890) or sulfinates (German Published Specification DOS No. 1.644.578 = British Patent Specification No. 1.053.455).

The process according to the invention is explained in more detail with the aid of the examples which follow.

EXAMPLE 1

2,700 g of technical grade (95% pure) 1-chloroanthraquinone are melted in a casserole. After adding 1,800 g of technical grade (95% pure) 1-nitroanthraquinone, the mixture is heated until a melt of low viscosity has formed (about 220° C). The melt thus obtained is poured, while simultaneously flushing with nitrogen, into a thermostat-controlled 4 l beaker (stainless steel) which has a ground top flange and which is fitted with a drain valve at the bottom, a rapid stirrer and an inlet tube provided with a frit. A rapid stream of chlorine (75 l/hour) is then passed into the melt, which is heated to 240° C, in such a way that the chlorine gas is finely dispersed in the reaction mixture. The course of the reaction is checked by taking a sample from the melt at regular set intervals (for example every 15 minutes) and powdering and analyzing this sample (by thin layer chromatography, gas chromatography and/or column chromatography).

The reaction is complete as soon as the evolution of nitrous gases ceases (about 90 minutes). Thereafter, the melt at 240° C, in the reaction vessel, is blown free from chlorine by passing in nitrogen and is then poured onto an enamelled metal sheet, where the melt is allowed to solidify. In this way, 4,340 g of a product, which contains 93% of 1-chloroanthraquinone and which is free from 1-nitroanthraquinone, are obtained.

1-Chloroanthraquinone is also obtained in good yield and in high purity when the procedure is as indicated above but the reaction temperature, the speed of the stream of chlorine and the reaction time are changed in the manner indicated in the table which follows.

(Table 1)

| Example | °C | Cl₂ (l/hour) | Time (minutes) | Yield (%) | 1-Chloroanthraquinone content in % |
|---|---|---|---|---|---|
| a | 240 | 75 | 90 | 96 | 93 |
| b | 250 | 24 | 140 | 93 | 92 |
| c | 250 | 48 | 100 | 89 | 87 |

Substantially similar results are obtained using 1-bromoanthraquinone as diluent and bromine as the halogenating agent.

EXAMPLE 2

A mixture of 700 g of 1,5-dichloroanthraquinone and 300 g of 1,5-dinitroanthraquinone is melted (at about 300° C), while passing in nitrogen, in a glass reaction vessel (length 300 mm, diameter 60 mm), which is heated to 300° C and which has a bottom frit (D2). The melt is then exhaustively chlorinated (24 l/hour). 870 g of 1,5-dichloroanthraquinone (84%) are obtained.

If the procedure is as indicated above but the mixtures of nitroanthraquinones indicated in the table which follows are used, the corresponding halogenoanthraquinones are obtained, under the indicated conditions, in the excellent yields quoted.

(Table 2)

| Example | Charge | Temperature (°C) | Cl₂ (l/hour) | Time (minutes) | Result |
|---|---|---|---|---|---|
| 3 | 700 g of 1,5-DCA + 300 g of 1,5-DNA | 300 | 24 | 40 | 870 g of 1,5-DCA (83.6% strength) |
| 4 | 700 g of 1,8-DCA + 300 g of 1,8-DNA | 265 | 24 | 50 | 940 g of 1,8-DCA (82.5% strength) |
| 5 | 700 g of 1-CA + 300 g of DNA mixture *) | 240 | 48 | 40 | 950 g of a DCA mixture **) |
| 6 | 1,000 g of 1-nitro-6-chloro-A | 260-5 | 24 | 120 | 890 g of 1,6-DCA (83% strength) |
| 7 | 700 g of 1-CA + 300 g of 1-oxy-4NA | 270 | 24 | 25 | 933 g of 1-CA and 1-chloro-4-oxy-A |
| 8 | 700 g of 1-CA + 300 g of 1-methoxy- | 275 | 24 | 25 | 835 g of 1-CA and 1-chloro-4- |

(Table 2)-continued

| Example | Charge | Temperature (° C) | Cl₂ (1/hour) | Time (minutes) | Result |
|---|---|---|---|---|---|
| 9 | 4-NA 700 g of 1-CA + 300 g of 1-chloro-2-NA | 260 | 24 | 25 | oxy A 953 g of 1-CA and 1,2-DCA |
| 10 | 400 g of 1,4,5-trichloro-A + 90 g of 1-nitro-4,5-DCA | 260–75 | 24 | 20 | 449 g of 1,4,5-trichloro-A |
| 11 | 700 g of 1-CA + 300 g of 1-NA-2-carboxylic acid | 275 | 24 | 25 | 950 g of a mixture 1-CA and A-2-carboxylic acid |

\* Consisting of 41% of 1,6-DNA, 39% of 1,7-DNA, 2% of 1,5-DNA and 17% of 1,8-DNA
\*\* This is free from nitroanthraquinone and can be separated according to known methods.
A = anthraquinone
CA = chloroanthraquinone
DCA = dichloroanthraquinone
NA = nitroanthraquinone
DNA = dinitroanthraquinone

EXAMPLE 12

1-Chloroanthraquinone in the molten state is initially introduced into a multi-stage bubble column which consists of 9 sections (length 200 mm, diameter 100 mm) and which is fitted with sieve trays and overflow pipes, and heated to 240° C. Technical grade 1-nitroanthraquinone together with 1-chloroanthraquinone is then metered into this melt, while passing in chlorine at the same time. The melt and the gas move in countercurrent, the mixture of chloroanthraquinone and nitroanthraquinone being fed in at the top of the column, while the chlorine is metered in in the lower part of the column. The concentration of chloroanthraquinone in the mixture fed to the column is about 20% by weight and its concentration in the overflow from the first section is about 22 – 24%. Nitrogen is blown in below the feed point for the chlorine in order to expel residual chlorine from the melt which is flowing down.

The mixture of chloroanthraquinone and nitroanthraquinone and the chlorine is so metered in that the nitroanthraquinone is fully reacted during its residence time in the apparatus and the conversion of the chlorine is virtually quantitative. The chloroanthraquinone which has formed is drawn off continuously via a siphon and solidified on a flaking drum.

1-Chloroanthraquinone is obtained in high purity in this way also.

EXAMPLE 13

A mixture of 80 g 1-bromoanthraquinone and 40 g 1-nitroanthraquinone is heated up to 240° C in a glass reaction vessel (length 20 cm, diameter 3 cm) with a porous plug at the bottom as gas inlet while a slow nitrogen stream bubbles through the melt. When temperature is reached, 5 ml of bromine are slowly vaporated by dopping it into a heated tube and passed through the melt. After 30 minutes all the 1-nitroanthraquinone has reacted and only 1-bromoanthraquinone remains (95 g after recristallisation from nitrobenzene).

It will be appreciated that the instant specification and examples are set forth by way of illustration and not limitation, and that various modifications and changes may be made without departing from the spirit and scope of the present invention.

What is claimed is:
1. A process for the preparation of a chloroanthraquinone or a bromoanthraquinone comprising forming a molten mixture of at least one nitroanthraquinone and diluent at a temperature of about 180° to 300° C, the diluent being in at least about 10% by weight of the mixture comprising at least one chloroanthraquinone or bromoanthraquinone, and thereafter adding halogen to said melt.

2. A process according to claim 1 wherein the halogen is chlorine and the diluent comprises at least one chloroanthraquinone.

3. A process according to claim 1 wherein the diluent is inert under the reaction conditions.

4. A process according to claim 1 wherein the diluent corresponds to the compound obtained from the nitroanthraquinone by replacing the nitro group with halogen.

5. A process according to claim 2 wherein the nitroanthraquinone comprises 1-nitroanthraquinone and the diluent comprises 1-chloroanthraquinone.

6. A process according to claim 2 wherein the nitroanthraquinone comprises 1,5-dinitroanthraquinone and the diluent comprises 1,5-dichloroanthraquinone.

7. A process according to claim 2 wherein the nitroanthraquinone comprises 1,8-dinitroanthraquinone and the diluent comprises 1,8-dichloroanthraquinone.

8. A process according to claim 1 wherein the nitroanthraquinone comprises a mixture of mononitroanthraquinones and dinitroanthraquinones obtained from industrial nitration of anthraquinone.

9. A process according to claim 1, carried out continuously.

10. A process according to claim 9, carried out continuously in a bubble column.

11. A process according to claim 1, wherein the melt is at a temperature of about 220° to 280° C.

12. A process according to claim 1, wherein the melt is at a temperature of about 240° to 280° C.

13. A process according to claim 4, carried out continuously in a bubble column at a temperature of about 240° to 280° C, and the concentration of chloroanthraquinone or bromoanthraquinone in the molten mixture where it is first contacted by halogen is at least about 50% by weight.

* * * * *